(12) United States Patent
Thiagarajan et al.

(10) Patent No.: US 7,816,576 B2
(45) Date of Patent: Oct. 19, 2010

(54) METHOD FOR CATALYTICALLY DEHYDRATING HYDROCARBONS

(75) Inventors: Natarajan Thiagarajan, Dortmund (DE); Max Heinritz-Adrian, Muenster (DE); Sascha Wenzel, Bochum (DE); Johannes Menzel, Waltrop (DE)

(73) Assignee: UHDE GmbH, Dortmund (DE)

( * ) Notice: Subject to any disclaimer, the term of this patent is extended or adjusted under 35 U.S.C. 154(b) by 695 days.

(21) Appl. No.: 10/532,843

(22) PCT Filed: Oct. 28, 2003

(86) PCT No.: PCT/EP03/11948

§ 371 (c)(1), (2), (4) Date: Dec. 19, 2005

(87) PCT Pub. No.: WO2004/039920

PCT Pub. Date: May 13, 2004

(65) Prior Publication Data
US 2006/0122448 A1     Jun. 8, 2006

(30) Foreign Application Priority Data
Oct. 31, 2002   (DE)   ................................ 102 51 135

(51) Int. Cl.
*C07C 5/333*   (2006.01)
(52) U.S. Cl. ................ 585/659; 585/412; 585/441; 585/443; 585/444; 585/445; 585/654; 585/655; 585/658; 585/660; 585/661
(58) Field of Classification Search ......... 585/658–660, 585/412, 441, 443, 444, 445, 654, 655, 661
See application file for complete search history.

(56) References Cited

U.S. PATENT DOCUMENTS

| | | | |
|---|---|---|---|
| 3,972,954 A * | 8/1976 | Bertus ........................ | 585/622 |
| 4,599,471 A | 7/1986 | Ward | |
| 4,739,124 A | 4/1988 | Ward | |
| 4,886,928 A | 12/1989 | Imai et al. | |
| 5,235,121 A | 8/1993 | Brinkmeyer et al. | |
| 5,321,192 A * | 6/1994 | Cottrell et al. ............. | 585/659 |
| 5,527,979 A | 6/1996 | Agaskar et al. | |
| 5,997,826 A | 12/1999 | Lodeng et al. | |

FOREIGN PATENT DOCUMENTS

| | | |
|---|---|---|
| DE | 19858747 A1 | 6/2000 |
| EP | 0 799 169 | 6/1996 |
| WO | WO 96/19424 A1 | 6/1996 |
| WO | WO 96/33150 A1 | 10/1996 |

* cited by examiner

*Primary Examiner*—Prem C Singh
(74) *Attorney, Agent, or Firm*—Marshall & Melhorn, LLC

(57) ABSTRACT

The invention relates to a method for producing unsaturated hydrocarbons. According to said method, in a first step, a hydrocarbon, especially a mixture which contains alkanes, essentially no water, and can contain water vapour, is continuously guided through a first catalyst bed provided with standard dehydration conditions. Liquid water, water vapour and a gas containing oxygen are then added to the reaction mixture obtained in the first step and, in a second step, the reaction mixture obtained is then continuously guided through another catalyst bed for oxidising hydrogen and for further dehydrating hydrocarbons. The first catalyst bed can be heated and the heating in the first step is then preferably regulated in such a way that an essentially isothermic operating mode is created.

12 Claims, 2 Drawing Sheets

METHOD FOR CATALYTICALLY DEHYDRATING HYDROCARBONS

BACKGROUND OF THE INVENTION

The catalytic dehydration of hydrocarbons according to the formula:

$$C_nH_{2n+2} \leftrightarrows C_nH_{2n} + H_2 \quad (1)$$

which as a rule takes place in the gaseous phase at a temperature between 540° C. and 820° C., is a highly endothermic equilibrium reaction the conversion rate of which is limited by the thermodynamics and depends on the respective partial pressures and the temperature. A dehydration reaction is facilitated by low partial pressures of the hydrocarbons and high temperatures. The side reactions leave cracked products, which form hydrocarbon deposits and cause a catalyst deactivation so that the catalyst must be periodically regenerated during plant operation.

If the dehydration takes place in an adiabatically operated catalyst bed, the endothermic reaction entails a gradual drop in temperature over the length of the catalyst bed. Hence, the conversion rate obtained in the catalyst bed is restricted so that the high rates envisaged necessitate several catalyst beds and re-heating downstream of each catalyst bed.

A catalytic dehydration of paraffins to obtain olefins may also take place in a heated, i.e. isothermic catalyst bed. U.S. Pat. No. 5,235,121, for example, describes a process which uses an input mixture consisting of light paraffins and water vapour and being fed to a tubular reactor with external firing system, i.e. the catalyst bed is a heated fixed bed. The catalyst used is designed in such a manner that a steam reforming process cannot take place in the presence of water vapour, i.e. no reaction of hydrocarbons with water vapour, forming CO, $CO_2$ and $H_2$. The catalyst is regenerated in cyclic intervals. Patent DE 198 58 747 A1 describes a similar process.

Heating the catalyst bed or the isothermic mode of operation (MO) permit very high conversion rates in a bulk catalyst bed. This MO, however, involves a disadvantage because the said rates, which are due to the level of the thermodynamic equilibrium, can be obtained at very high temperatures only, a fact that reduces the selectivity of olefin formation.

The a/m MO in the presence of water vapour bears the advantage that the partial pressure of the hydrocarbons is reduced by the water vapour and thus contributes to a higher conversion rate. Moreover, the utilisation of water vapour permits the conversion of a certain part of hydrocarbons to $CO_2$ on the catalyst so that the cycle times, i.e. operating periods of dehydration between the regeneration cycles, can be prolonged. But it is true that too large quantities of water vapour are detrimental to the process as there is a substantial increase in the gas stream volume which entails additional investment costs and impedes the process efficiency. Furthermore this increases the risk of steam reforming of hydrocarbons, which leads to the loss of product and/or reduces the yield. The quantity of steam the can be added without causing the problems described above depends on the absolute pressure applied in the reaction process and on the dehydration catalyst itself.

There is a further possibility of overcoming the thermodynamic limitation of the conversion at equilibrium, i.e. by feeding oxygen to selectively burn a portion of the hydrogen obtained by dehydration in accordance with $$2 H_2 + O_2 \rightarrow 2 H_2O \quad (2)$$

—a process step also named "SHC" short for "Selective Hydrogen Combustion"—so that the equilibrium of the dehydration is re-arranged such that higher conversion rates become feasible. Patent EP 0 799 169 B1 describes a reactor for such a dehydration process with SHC, a mixture of paraffin and oxygen being sent via a first catalyst which performs dehydration and selective oxidation of the hydrogen obtained, a further admixture of oxygen taking place in an intermediate reactor chamber and finally, there is a second catalyst that also performs dehydration and selective oxidation of the hydrogen obtained. The process described in EP 0 799 169 B1 takes place in an autothermal mode and the highly exothermic reaction (2) of the hydrocarbon with oxygen supplies the energy required to carry out the endothermic dehydration reaction (1).

Patent WO 96/33150, for example, describes a process in which the paraffin mixture is first dehydrated in a primary step, oxygen then being added and this oxygen reacting at least in a secondary step with the hydrogen released by dehydration so that water vapour is obtained. At least a part stream of the product obtained undergoes a secondary dehydration in order to dehydrate the paraffins not yet converted; recycling of a part stream to the primary step is also suggested.

The disadvantage of the process is that the addition of oxygen and the exothermic oxidation of hydrogen lead to very high temperatures, which reduces the selectivity of the downstream catalytic dehydration. This particularly applies to isothermic dehydration in the first step because in the case of adiabetic dehydration carried out in the first step, the temperature drop occurring in the catalyst bed causes an input temperature towards the SHC step that is lower than that in the case of isothermic dehydrations.

The problem of superheating due to hydrogen oxidation can be solved by intermediate cooling that takes place before the selective hydrogen oxidation and thus reduces the temperature at the inlet of the second catalyst bed. U.S. Pat. No. 4,599,471, for example, suggests such an intermediate cooling either of the direct or indirect type. The direct cooling is feasible with the aid of inert gas such as nitrogen, helium, etc. or steam.

Temperature control through indirect cooling, however, has a disadvantage because it requires firmly installed heat exchangers, which does not permit specific temperature guidance for catalyst bed regeneration, or it necessitates a circuitry for intermittent uncoupling of the heat exchanger, for example, by means of a by-pass that can be shut down by additional valves. This configuration, however, would be extremely expensive on account of the large pipe cross-sections and the high operating temperatures of approx. 500-650° C. due to the dehydration.

Direct cooling with the aid of inert gases bears a disadvantage because later they must be separated from the product in expensive steps in order to further process the product. Indirect cooling with the aid of steam has a disadvantage since in the reaction as described above is not inert and develops a certain steam-to-hydrocarbon ratio depending on the cooling. Hence, the steam quantity considerably increases with the cooling intensity, which is detrimental to the process, i.e. it becomes evident through an increase in the construction scope and the probability of an undesired steam reforming of hydrocarbons.

SUMMARY OF THE INVENTION

The aim of the invention, therefore, is to provide a process layout that permits dehydration with subsequent hydrogen oxidation and further dehydration, the said layout being suitable for direct cooling of the intermediate stream prior to hydrogen oxidation, thus permitting a simple separation of the coolant during product treatment on the one hand, and the avoidance of detrimental impacts of the coolant on the downstream dehydration on the other hand.

In accordance with the main claim, the invention provides for a technical solution set forth below:

in a first step hydrocarbon, in particular a mixture containing alkanes, which may have a water vapour content but which is essentially free from oxygen, flows in a continuous stream through the first catalyst bed, the latter exhibiting the standard dehydration conditions;

in a subsequent stage the reaction mixture obtained in the first step and mainly consisting of alkanes, alkenes, water vapour, hydrogen and by-products is mixed with liquid phase water and water vapour as well as with an oxygen-bearing gas;

the reaction mixture thus obtained is subsequently fed in a continuous stream to a further catalyst bed as second step in which hydrogen oxidation and further dehydration of hydrocarbons take place.

An embodiment of the invention provides for a heated first catalyst bed that is preferably operated in an almost isothermal mode, the equipment design being similar to the configuration described in U.S. Pat. No. 5,235,121.

The addition of liquid phase water and water vapour prior to the selective hydrogen oxidation permits the simultaneous and independent adjustment of the optimal temperature and of a specific $H_2O$/hydrocarbon ratio in the gas phase, the evaporation heat of the added liquid phase water that completely evaporates playing a major role for temperature adjustment. Water vapour can be easily separated by condensation in further process steps. The specific adjustment of the $H_2O$/hydrocarbon ratio in the gas phase avoids a steam quantity that would be detrimental to the process, in particular a steam reforming of hydrocarbons or too large a volumetric flow of gas resulting from too much steam or in the case of too small a steam amount, the formation of too much hydrocarbon deposits or too high hydrogen partial pressures in the reacting gas.

A further embodiment of the invention provides for the mixture of an oxygen-bearing gas with the reaction mixture obtained in the second step and for the reaction mixture thus obtained to be passed in a continuous mode through at least a third step having another catalyst bed, which contains a similar or the same catalyst material as in the upstream process steps. This layout permits a gradual addition of oxygen in the individual steps in order to minimise the oxygen concentration detrimental to the product.

In a further embodiment of the invention the catalyst bed of the first step uses any standard commercial dehydration catalyst. For the second and any further catalyst bed it is imperative to provide dehydration catalysts that exhibit not only dehydration activity but also SHC activity.

Such noble metal bearing catalysts applied to adequate carrier materials are, for example, $Al_2O_3$, $SiO_2$, $ZrO_2$, zeolite, hydrotalcite, $CaAl_2O_4$, $ZnAl_2O_4$, $MgAl_2O_4$ or mixtures thereof. Said materials may be alloyed with further components such as those of group IV A of the periodic system or of group I A, but also dehydration catalysts based on transition metal oxide such as catalysts on the basis of $Fe_2O_3$, $Cr_2O_3$, $MoO_3$ or $V_2O_5$ are appropriate within the meaning of the invention.

In a further embodiment of the invention any of the steps, particularly the second and further steps, if any, can be equipped with a catalyst that contains Pt and Sn applied to a carrier element that essentially contains aluminate, in particular Zn aluminate.

A further embodiment of the invention provides for a specialist catalyst mounted in the bed of the second and further steps (if any) and is intended for hydrogen oxidation, hence a catalyst that improves the selectivity compared to the that of dehydration catalysts when hydrogen oxidation takes place, said specialist catalysts being employed in combination with the dehydration catalysts.

A further embodiment of the invention provides for a cooling of the reaction mixture downstream of the second step prior to conveying the mixture to a further catalyst bed in a third step. When this configuration encompasses further steps, such an inter-cooling may also be arranged between two steps each. Indirect cooling may also be provided in order to exploit the recovered heat for pre-heating the input mixture before it enters the first step. Water and water vapour have to be added accordingly if and when required. A cooling provided upstream of the second and any further step has the advantage that the velocity of side-reactions is reduced when oxygen is added, thus obtaining a higher selectivity.

In a further embodiment of the invention the oxygen-bearing gas is air rich in oxygen, e.g. with an oxygen content of 90 to 95%. This permits smaller equipment sizes compared to those fed with air. On the other hand, the admixture of air has the advantage that the partial pressures of the hydrocarbons decline and the equilibrium conversion increases; air is also cheaper.

In another embodiment of the invention the quantity of oxygen-bearing gas added in the second or further steps is controlled via the temperature measured at the outlet of the respective upstream catalyst bed or via the outlet temperature of the last catalyst bed.

BRIEF DESCRIPTION OF THE DRAWINGS

The invention is illustrated on the basis of two examples.

DESCRIPTION OF THE PREFERRED EMBODIMENT

Figure 1:
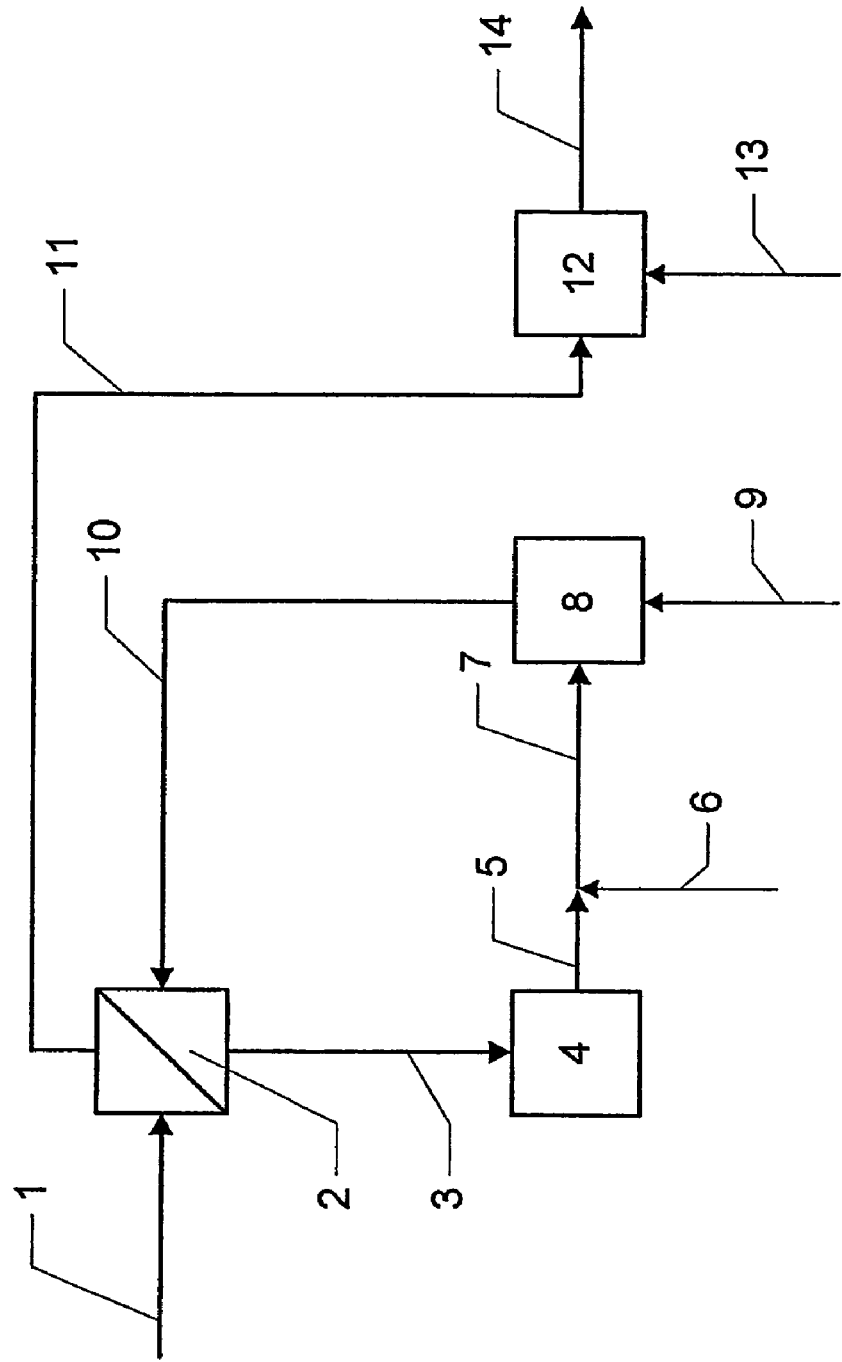
FIG. 1 shows the process according to the invention in a three-step layout with inter-cooling.

FIG. 1: Input mixture 1 that consists of propane and water vapour is heated in gas-gas heat exchanger 2 to obtain a temperature of 550° C. The heated input mixture 3 is piped to dehydration step 4 where part of the propane reacts to form propylene. The heater is set such that the temperature at the outlet of dehydration step 4 is as high as 570° C. A defined mixture of water and water vapour 6 is added to reaction mixture 5 so that mixture 7 cools down to 510° C. and the ratio of water vapour and hydrocarbons is precisely adjusted in dehydration step 8.

Mixture 7 is conveyed to dehydration step 8 and a specific quantity of oxygen-rich air 9 is added to the mixture directly before entering the catalyst bed of said step. Product mixture 10 thus obtained has a temperature of 590° C. and a certain part of its heat is transferred to input mixture 1 in gas/gas heat exchanger 2. Product mixture 11 leaves said exchanger 2 at a temperature of 510° C. and is fed to dehydration step 12, oxygen-rich air 13 being added directly before the catalyst bed of the said step. Product gas 14 obtained is piped to the downstream units for treatment. A standard dehydration catalyst is employed in all dehydration steps.

Figure 2:
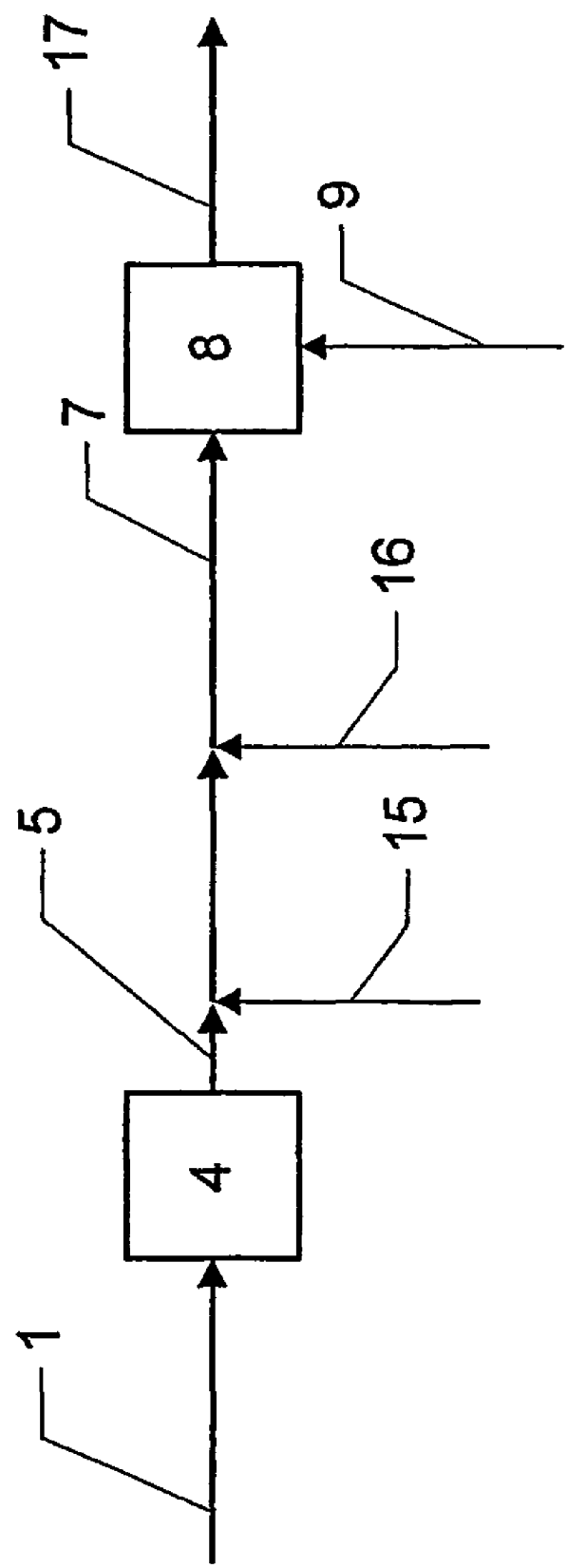
FIG. 2 shows a two-step configuration according to the invention.

FIG. 2: Input mixture 1 that consists of propane and water vapour is fed to dehydration step 4 where part of the propane reacts to form propylene. Liquid phase water 15 and water vapour 16 are added to reaction mixture 5, which permits a precise adjustment of the ratio of water vapour and hydrocarbons in dehydration step 8. Mixture 7 is fed to dehydration step 8, oxygen-rich air 9 being admixed directly before the catalyst bed of said step. Product mixture 17 thus obtained is piped to the downstream units for treatment. A standard dehydration catalyst is employed in all dehydration steps.

Two typical process calculation examples were chosen for further illustration of the process embodiment shown in FIG. 2, the gas constituents from side reactions or impurities such as $CO_2$, $CH_4$, $N_2$ being named "Others".

PROCESS CALCULATION EXAMPLE 1

|  |  | Stream No. | | | | | | |
| --- | --- | --- | --- | --- | --- | --- | --- | --- |
|  |  | 1 | 5 | 7 | 9 | 15 | 16 | 17 |
| Temperature | [° C.] | 550 | 580 | 532 | 180 | 180 | 240 | 580 |
| Pressure | [bar] | 9 | 6 | 5.9 | 8 | 12 | 12 | 5 |
| Oxygen $O_2$ | [kg/h] |  |  |  | 7344 |  |  |  |
| Hydrogen $H_2$ | [kg/h] |  | 2514 | 2514 |  |  |  | 3439 |
| Steam $H_2O$ | [kg/h] | 176845 | 175017 | 210387 |  |  | 26730 | 215635 |
| Liquid $H_2O$ | [kg/h] |  |  |  |  | 8640 |  |  |
| Propane $C_3H_8$ | [kg/h] | 123511 | 86458 | 86458 |  |  |  | 74106 |
| Others | [kg/h] | 2470 | 4883 | 4883 | 714 |  |  | 9687 |
| Propene $C_3H_6$ | [kg/h] |  | 33954 | 33954 |  |  |  | 43387 |

PROCESS CALCULATION EXAMPLE 2

|  |  | Stream No. | | | | | | |
| --- | --- | --- | --- | --- | --- | --- | --- | --- |
|  |  | 1 | 5 | 7 | 9 | 15 | 16 | 17 |
| Temperature | [° C.] | 550 | 575 | 486 | 180 | 115 | 180 | 600 |
| Pressure | [bar] | 6 | 2 | 1.9 | 12 | 4 | 4 | 1.1 |
| Oxygen $O_2$ | [kg/h] |  |  |  | 10098 |  |  |  |
| Hydrogen $H_2$ | [kg/h] |  | 3306 | 3306 |  |  |  | 5271 |
| Steam $H_2O$ | [kg/h] | 50527 | 47628 | 67839 |  |  | 4010 | 73089 |
| Liquid $H_2O$ | [kg/h] |  |  |  |  | 16201 |  |  |
| Propane $C_3H_8$ | [kg/h] | 123511 | 80282 | 80282 |  |  |  | 65461 |
| Others | [kg/h] | 2470 | 6091 | 6091 | 465 |  |  | 13591 |
| Propene $C_3H_6$ | [kg/h] |  | 39201 | 39201 |  |  |  | 49870 |

LIST OF REFERENCES USED

| 1 | Input mixture |
| --- | --- |
| 2 | Gas/gas heat exchanger |
| 3 | Heated input mixture |
| 4 | Dehydration step |
| 5 | Reaction mixture |
| 6 | Liquid phase water/water vapour mixture |
| 7 | Mixture |
| 8 | Dehydration step |
| 9 | Oxygen-rich air |
| 10 | Product mixture |
| 11 | Product mixture |
| 12 | Dehydration step |
| 13 | Oxygen-rich air |
| 14 | Product gas |
| 15 | Liquid phase water |
| 16 | Water vapour |
| 17 | Product mixture |

The invention claimed is:

1. A process for the production of unsaturated hydrocarbons, with the following layout:

In a first step a hydrocarbon comprising paraffins, which may have a water vapor content but which is essentially free from oxygen, penetrates in a continuous stream through a first catalyst bed, the latter exhibiting the standard dehydration conditions;

subsequently the reaction mixture obtained in the first step is mixed with liquid phase water and water vapor as well as with an oxygen-bearing gas;

and then the reaction mixture is fed in a continuous stream to a further catalyst bed as a second step in which hydrogen oxidation and further dehydration of the hydrocarbons take place.

2. The process according to claim 1, wherein the first catalyst bed is heated and the heating of the first step is preferably adjusted in such a manner that an essentially isothermal operating mode is obtained.

3. The process according to claim 1, wherein oxygen-bearing gas is added to the reaction mixture produced in the second step and the reaction mixture thus obtained flows in a continuous stream through a further catalyst bed in at least a third step.

4. The process according to claim 1, wherein the reaction mixture is cooled in a cooling unit downstream of the second step prior to entering a further catalyst bed in a third process step.

5. The process according to claim 1, wherein the catalyst bed of the first step uses any standard commercial dehydration catalyst and the second and any further catalyst bed are provided with dehydration catalysts that exhibit not only dehydration activity but also SHC activity.

6. The process according to claim 2, comprising a catalyst that contains Pt and Sn applied to a carrier element essentially containing aluminate.

7. The process according to claim 2, comprising a specialist catalyst for water oxidation, hence a catalyst that improves the selectivity compared to that of standard dehydration catalysts when it comes to hydrogen oxidation, the said specialist catalysts being employed in combination with standard dehydration catalysts.

8. The process according to claim 1, wherein the oxygen-bearing gas is oxygen-rich air.

9. The process according to claim 1, wherein the quantity of oxygen-bearing gas added in the second and further steps is controlled via the temperature measured at the outlet of the respective upstream catalyst bed or via the outlet temperature of the last catalyst bed.

10. The process according to claim 1, wherein the hydrocarbon comprises a mixture containing alkanes.

11. The process according to claim 6, wherein the aluminate comprises zinc aluminate.

12. A process for the production of unsaturated hydrocarbons, with the following layout:
   In a first step a hydrocarbon comprising paraffins, which may have a water vapor content but which is essentially free from oxygen, penetrates in a continuous stream through a first catalyst bed, the latter exhibiting the standard dehydration conditions;
   subsequently the reaction mixture obtained in the first step is mixed with liquid phase water and water vapor as well as with an oxygen-bearing gas, wherein the water and water vapor introduction decreases the reaction temperature;
   and then the reaction mixture is fed in a continuous stream to a further catalyst bed as a second step in which hydrogen oxidation and further dehydration of the hydrocarbons take place.

* * * * *